United States Patent
Taniguchi

(10) Patent No.: US 9,603,356 B2
(45) Date of Patent: Mar. 28, 2017

(54) METHOD FOR PRODUCING CELL CONCENTRATE

(71) Applicant: KANEKA CORPORATION, Kita-ku (JP)

(72) Inventor: Shuhei Taniguchi, Settsu (JP)

(73) Assignee: KANEKA CORPORATION, Kita-ku (JP)

(*) Notice: Subject to any disclaimer, the term of this patent is extended or adjusted under 35 U.S.C. 154(b) by 130 days.

(21) Appl. No.: 14/353,119

(22) PCT Filed: Oct. 18, 2012

(86) PCT No.: PCT/JP2012/076964
§ 371 (c)(1),
(2) Date: Apr. 21, 2014

(87) PCT Pub. No.: WO2013/061859
PCT Pub. Date: May 2, 2013

(65) Prior Publication Data
US 2014/0287502 A1    Sep. 25, 2014

(30) Foreign Application Priority Data

Oct. 24, 2011 (JP) .................................. 2011-232871

(51) Int. Cl.
*A01N 1/02* (2006.01)
*B01D 71/26* (2006.01)
(Continued)

(52) U.S. Cl.
CPC ............ *A01N 1/0284* (2013.01); *B01D 63/02* (2013.01); *B01D 71/26* (2013.01); *B01D 71/68* (2013.01);
(Continued)

(58) Field of Classification Search
CPC ...... A01N 1/0284; B01D 63/02; B01D 71/26; B01D 71/68; B01D 2323/02;
(Continued)

(56) References Cited

U.S. PATENT DOCUMENTS 3,852,155 A * 12/1974 Moore ...................... A61L 2/02
424/207.1
6,010,627 A * 1/2000 Hood, III ............... A61K 35/14
210/321.6

(Continued)

FOREIGN PATENT DOCUMENTS

CN          1231212 A       10/1999
EP          1 683 857 A1     7/2006
(Continued)

OTHER PUBLICATIONS

Weiss et al. Improved Method for the Production of Insect Cell Cultures in Large Volume. In Vitro (1981), v17(6), p. 495-502.*
(Continued)

*Primary Examiner* — Scott Long
*Assistant Examiner* — Sean C Barron
(74) *Attorney, Agent, or Firm* — Oblon, McClelland, Maier & Neustadt, L.L.P.

(57) ABSTRACT

The present invention provides a method that allows the preparation of a cell concentrate in a short time without loss of cells and great damage on cells by simple operations. The present invention provides a method for producing a cell concentrate using an inside-out filtration system for processing a cell suspension, the system including: a cell suspension inlet port; a filtrate outlet port; a cell suspension outlet port; and a hollow fiber separation membrane interposed between the cell suspension inlet port and the cell suspension outlet port, wherein the hollow fiber separation membrane is provided with inner pores with an average pore size of 0.1

(Continued)

μm to 10 μm, and the quotient of the division of an initial filtrate flow rate by a linear velocity of the cell suspension flowing through the hollow fibers is 2.5 or less.

10 Claims, 1 Drawing Sheet

(51) Int. Cl.
  *B01D 71/68* (2006.01)
  *C12N 5/07* (2010.01)
  *B01D 63/02* (2006.01)
  *C12N 1/02* (2006.01)
  *C12N 1/04* (2006.01)

(52) U.S. Cl.
  CPC .................. *C12N 1/02* (2013.01); *C12N 1/04* (2013.01); *C12N 5/06* (2013.01); *B01D 2323/02* (2013.01); *B01D 2325/20* (2013.01)

(58) Field of Classification Search
  CPC ... B01D 2325/20; C12M 47/02; C12M 47/12; C12N 1/02; C12N 1/04; C12N 5/06
  USPC ......................................... 435/374
  See application file for complete search history.

(56) References Cited

U.S. PATENT DOCUMENTS

| | | | |
|---|---|---|---|
| 2013/0280767 | A1 | 10/2013 | Kobayashi et al. |
| 2014/0287502 | A1 | 9/2014 | Taniguchi |

FOREIGN PATENT DOCUMENTS

| | | |
|---|---|---|
| EP | 2 335 814 A1 | 6/2011 |
| JP | 63-160578 A | 7/1988 |
| JP | 06-098758 A | 4/1994 |
| JP | 2928913 B2 | 5/1999 |
| JP | 2928913 B2 | 8/1999 |
| JP | 2003-319774 A | 11/2003 |
| JP | 2005-336080 A | 12/2005 |
| JP | 2006-129987 A | 5/2006 |
| JP | 2006-305333 A | 11/2006 |
| JP | 2007-524396 A | 8/2007 |
| JP | 2008-229612 A | 10/2008 |
| WO | WO 2004/004873 A1 | 1/2004 |
| WO | WO 2011/091248 A1 | 7/2011 |
| WO | WO 2011/091248 A8 | 7/2011 |
| WO | WO 2012/090863 A1 | 7/2012 |
| WO | WO 2013/061859 A1 | 5/2013 |

OTHER PUBLICATIONS

U.S. Appl. No. 14/424,574, filed Feb. 27, 2015, Taniguchi.
English translation of the International Preliminary Report on Patentability issued May 8, 2014 in PCT/JP2012/076964.
English translation of the Written Opinion issued Dec. 25, 2012 in PCT/JP2012/076964.
International Search Report issued Dec. 25, 2012 in PCT/JP2012/076964.
Loc Trinh, et al., "Recovery of insect cells using hollow fiber microfiltration", Biotechnology and Bioengineering, vol. 48, No. 4 Nov. 20, 1995, pp. 401-405.
Joseph Shiloach, et al., "Hollow fiber microfiltration methods for recovery of rat basophilic leukemia cells (RBL-2H3) from tissue culture media", Biotechnology Progress, vol. 2, No. 4, Dec. 1986, pp. 230-233.
International Search Report issued Nov. 5, 2013 in PCT/JP2013/072056.
International Preliminary Report on Patentability and Written Opinion issued Mar. 3, 2015 in PCT/JP2013/072056.
F. Castino, et al., "Washing frozen red blood cell concentrates using hollow fibres" Journal of Membrane Science, vol. 110, 1996, pp. 169-180.

* cited by examiner

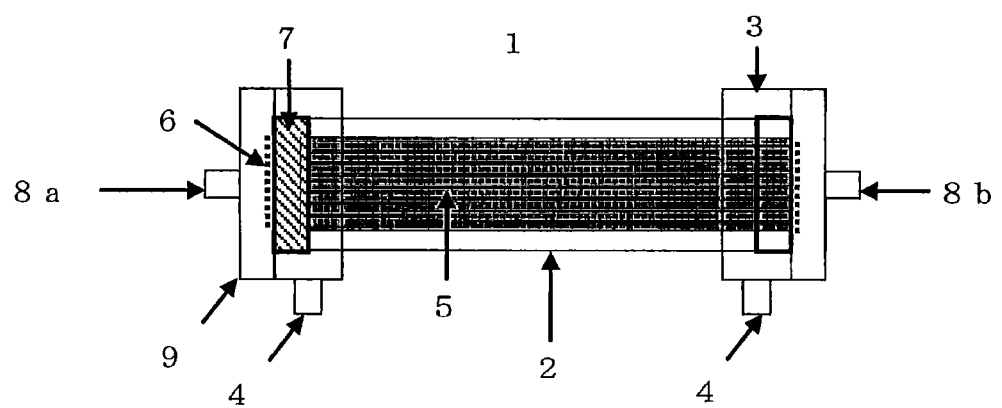

METHOD FOR PRODUCING CELL CONCENTRATE

TECHNICAL FIELD

The present invention relates to a technique for concentrating cells in cell suspensions. More specifically, the present invention relates to a method for producing a cell concentrate using a cell suspension processing system including a hollow fiber separation membrane.

BACKGROUND ART

Cell therapy employs a technique in which cells from a living donor are implanted into a subject either directly or after being cultured in vitro. Cells for use in implantation are suspended in a solution suitable for implantation, and adjusted to a suitable concentration prior to implantation. Cells taken from a living donor, optionally cultured in vitro, contain unnecessary tissue-derived components, culture media, and the like, and are typically available as dilutions in particular solutions. Accordingly, the following processes are necessary prior to implantation: removal of unnecessary components and media, and replacement with a solution suitable for implantation (washing); and concentration of cells to a level suitable for implantation. So far, centrifugation has been a principal technique used for such concentration and washing processes.

For example, a technique for separating and concentrating regenerative cells from human tissues by centrifugation is known (Patent Literature 1). Unfortunately, centrifugation is a technique that may be employed in a limited number of facilities because of the necessity of a large-scale device, a burden on cells, and high costs.

By contrast, compact, easy-to-handle devices have been designed for the separation, purification and filtration of cell suspensions using a hollow fiber separation membrane (Patent Literature 2).

Hollow fiber separation membranes proposed so far have various pore sizes, and appropriate sizes are chosen according to the size of target substances and the desired filtration flow rate. For example, hollow fibers with large pore sizes are used to achieve high filtration flow rate. Fibers with too large pore sizes, however, may cause pores to be clogged with proteins or cells present in samples, for example. Patent Literature 3 discloses hollow fiber products designed to overcome this. These products include hollow fibers with relatively large average pore sizes to provide a high filtration flow rate with the aim of high yields, while including in the hollow fibers an anionic resin to prevent clogging in pores. For safety reasons, hollow fibers including two or more materials, however, are not preferred for use in the concentration of cultured cells to be returned to the body because leakage of the materials and the like are likely to occur. Another approach for preventing clogging in pores is to employ certain washing/filtration conditions and the like (Patent Literature 4). Unfortunately, this approach is likely to greatly damage cells because of the necessity of backwashing of a hollow fiber membrane.

CITATION LIST

Patent Literature

Patent Literature 1: JP 2007-524396 T
Patent Literature 2: Japanese Patent No. 2928913
Patent Literature 3: JP 2008-229612 A
Patent Literature 4: JP H06-98758 A

SUMMARY OF INVENTION

Technical Problem

An object of the present invention is to solve the above problems in the production of cell concentrates using a hollow fiber separation membrane. Specifically, the present invention provides a method for producing a cell concentrate which can concentrate a cell suspension with efficient cell recovery maintained while preventing clogging in pores. Another object of the present invention is to provide a method for producing a cell concentrate which maintains efficient cell recovery, prevents clogging in pores, and causes less damage on cells.

Solution to Problem

Intensive studies to solve the above problems by the present inventor revealed that the above problems can be solved by using hollow fibers with relatively large pore sizes to ensure high filtration flow rate, and controlling the ratio between the initial rate of filtration and the linear velocity of a cell suspension flowing through the hollow fibers in a cell suspension processing system to fall within a certain range. Thus, the present invention was completed.

Specifically, the present invention relates to a method for producing a cell concentrate using an inside-out filtration system for processing a cell suspension, the system including: a cell suspension inlet port; a filtrate outlet port; a cell suspension outlet port; and a hollow fiber separation membrane interposed between the cell suspension inlet port and the cell suspension outlet port, wherein the hollow fiber separation membrane is provided with inner pores with an average pore size of 0.1 μm to 10 μm, and the quotient of the division of an initial filtrate flow rate by a linear velocity of the cell suspension flowing through the hollow fibers is 2.5 or less.

Preferably, the cell suspension flows through the cell suspension inlet port at a flow rate of 200 mL/min to 1200 mL/min.

Preferably, the hollow fiber separation membrane includes a synthetic polymer material.

Preferably, the hollow fiber separation membrane includes a polysulfone or polyolefin polymer material.

Preferably, the hollow fiber separation membrane includes polyethersulfone, polysulfone, or polyethylene.

Preferably, the cell suspension is an immune cell suspension.

The method for producing a cell concentrate preferably further includes the step of washing cells.

The present invention also relates to a method for growing cells, including the step of mixing a cell concentrate obtained by the above method with a medium.

The present invention further relates to a method for cryopreserving cells, including the step of cryopreserving a cell concentrate obtained by the above production method or the above cell growth method with liquid nitrogen.

Advantageous Effects of Invention

The present invention makes it possible to recover cells in a suspension at high efficiency while removing unnecessary components other than target cells, such as proteins, and to produce a cell concentrate while reducing clogging of hollow fibers with cells. Additionally, since clogging in pores can be prevented without any process that can impose a burden on cells (e.g. back-washing of a membrane), cells are less damaged, thereby increasing the viability of cells. Moreover, the present invention provides concentrated cells usable for cell therapy because cells can be processed in an aseptic closed system.

BRIEF DESCRIPTION OF DRAWINGS

FIG. 1 illustrates a cell suspension processing system used in Examples of the present invention.

DESCRIPTION OF EMBODIMENTS

The following description is offered to illustrate the present invention.

FIG. 1 illustrates a non-limiting example of a cell suspension processing system according to the present invention. A tubular housing 1 consists of a straight body 2, and a head 3 and a header 9 on the respective ends of the body. The head 3 and the header 9 are each provided with a filtrate outlet port 4. Filtrate outlet ports may be thus provided on both the ends, or only one filtrate outlet port may be provided on either end. In this shown example, the header 9 is provided with a cell suspension inlet port 8a, and the head 3 is provided with a cell suspension outlet port 8b. The inside of the tubular housing 1 is filled with a hollow fiber separation membrane bundle 5, and provided with a resin layer 7 within the header 9 and a similar structure to the resin layer 7 within the head 3. The resin layer 7 immobilizes the bundle 5 to the inside of the housing, and also forms an open end 6 of the hollow fiber separation membranes. The resin layer 7 and the open end 6 are capped with the header 9 (or the head 3), and the cell suspension inlet port 8a and the cell suspension outlet port 8b are separated from the filtrate outlet ports 4 by a wall member included in the hollow fiber separation membranes, so that they are not continuous.

Although, for convenience, the components of the tubular housing are distinguished from each other as, for example, body 2, head 3, and header 9 in the example shown in FIG. 1, the tubular housing may have any structure even when, for design requirements, the header 9 is integrated with the head 3 of the tubular housing, or the body 2 and the head 3 of the tubular housing are formed as separate components, provided that the cell suspension inlet port and the cell suspension outlet port are not separated by the wall member included in the hollow fiber separation membranes and are thus continuous, while these ports are separated from the filtrate outlet ports by the wall member included in the hollow fiber separation membranes.

The tubular housing of the cell suspension processing system according to the present invention is preferably filled with a bundle consisting of several tens to several thousands of hollow fiber separation membranes. In the present invention, the hollow fiber separation membranes may be disposed linearly, in a curved orientation, helically, or in any shape without limitation, provided that the ends of the hollow fiber separation membranes are interposed between the cell suspension inlet port and the cell suspension outlet port.

Preferred examples of materials for the tubular housing of the cell suspension processing system include acrylonitrile polymers, such as acrylonitrile-butadiene-styrene terpolymers; halide polymers, such as polytetrafluoroethylene, polychlorotrifluoroethylene, tetrafluoroethylene-hexafluoropropylene copolymers, and polyvinyl chloride; and polyamide, polyimide, polysulfone, polycarbonate, polyethylene, polypropylene, polyvinylchloride acrylic copolymers, polycarbonate/acrylonitrile-butadiene-styrene, polystyrene, and polymethylpentene. In particular, sterilization-resistant materials, such as block copolymers containing polypropylene, polyvinyl chloride, polyethylene, polyimide, polycarbonate, polysulfone, polymethylpentene, and/or polystyrene, are preferred.

Preferred examples of materials for the resin layer immobilizing the hollow fiber separation membranes include common adhesive materials, such as polyurethane resins, epoxy resins, and silicon resins.

The "inside-out filtration mode" herein refers to filtration in which a filtrate substantially free from cells passes through hollow fiber separation membranes from the inside to the outside thereof. The "filtrate substantially free from cells" herein refers to a filtrate in which the number of cells present therein is not more than 0.1% of that of the original cell suspension. For example, a cell suspension introduced into the cell suspension inlet port may be filtered to give a filtrate under water pressure that occurs when the cell suspension flows into the inside of the hollow fiber separation membranes in the cell suspension processing system, or negative pressure may be generated outside the hollow fiber separation membranes.

In the present invention, the hollow fiber separation membranes are preferably provided with inner pores with an average pore size of at least 0.05 μm but not more than 20 μm, more preferably at least 0.1 μm but not more than 10 μm, still more preferably at least 0.5 μm but not more than 10 μm. Pores with an average pore size of less than 0.1 μm may not provide sufficient filtration velocities, and may not efficiently remove unnecessary components, such as unnecessary proteins. Pores with an average pore size of more than 10 μm may undesirably reduce the cell recovery rate because target cells may be stuck in pores. The "average pore size" of the inner pores of the hollow fiber separation membranes refers to the average diameter of the largest 20 pores among pores that are observed within the range of 62 μm×43 μm or 25 μm×17 μm with a 2000× or 5000× scanning electron microscope.

The "initial filtrate flow rate" refers to the filtration velocity during the filtration of an initial 500 mL filtrate. The "filtration velocity" is defined as the quotient of the division of the amount of filtrate formed per unit time by the whole hollow fiber separation membranes by the filtration area. For example, the filtration velocity is determined by dividing the amount of filtrate passing through the filtrate outlet ports of the cell suspension processing system shown in FIG. 1 per unit time by the filtration area. The "filtration area" is calculated as follows: (filtration area)=(number of fibers)× π×(hollow fiber inner diameter)×(effective length).

The "linear velocity" is defined as the quotient of the division of the amount of fluid flowing into hollow fiber lumens per unit time by the cross-sectional area of the hollow fiber lumens. For example, the linear velocity is determined by dividing the amount of fluid passing through the cell suspension inlet port of the cell suspension processing system shown in FIG. 1 by the total cross-sectional area of the hollow fiber lumens in the cell suspension processing system.

In the method for producing a cell concentrate of the present invention, the quotient of the division of the initial filtrate flow rate by the linear velocity of a cell suspension is preferably not more than 3.0. In order to concentrate cells without a loss of cells, the quotient is more preferably 2.5 or less. In the case of a quotient of more than 3.0, the cell recovery rate tends to be low. The "cell recovery rate" refers to the quotient of the division of the total number of cells in a concentrated cell suspension by the total number of cells in the original cell suspension.

In the present invention, a cell suspension is preferably flowed at a rate of not lower than 100 mL/min and not higher than 1500 mL/min, more preferably not lower than 200 mL/min and not higher than 1200 mL/min, still more preferably not lower than 300 mL/min and not higher than 800 mL/min. If a cell suspension is flowed at a rate of lower than 200 mL/min, the filtration flow rate cannot be increased beyond a certain level without decreasing the cell recovery rate, and thus cells cannot be efficiently concentrated. If a cell suspension is flowed at a rate of higher than 1200 mL/min, higher pressure is required to deliver a large amount of cell suspension, and the cell suspension may generate strong shear force and pressure to damage cells during flowing through the path and hollow fibers. Accordingly, the recovery rate and viability of cells may be decreased.

Preferred examples of resin materials for hollow fiber separation membranes usable in the present invention include synthetic polymer materials because of their safety and stability. Among them, more preferred is a polysulfone or polyolefin polymer material. Most preferred is polyethersulfone, polysulfone, or polyethylene because of their safety, stability and availability.

The filtration area of the hollow fiber separation membranes used in the present invention is preferably in the range of from 0.01 to 1.0 $m^2$, more preferably from 0.02 to 1.0 $m^2$. If the filtration area is smaller than 0.01 $m^2$, sufficient filtration rate per unit time may not be ensured; if the filtration area is larger than 1.0 $m^2$, some of the cell suspension may remain in the hollow fiber separation membranes, resulting in low recovery and high costs.

In the present invention, the total cross-sectional area of the lumens of the hollow fiber separation membranes is preferably at least 0.1 $cm^2$ but not more than 3.0 $cm^2$, and more preferably at least 0.3 $cm^2$ but not more than 2.0 $cm^2$. If the total cross-sectional area is smaller than 0.1 $cm^2$, the linear velocity can be too high, and may lead to damage on cells. If the total cross-sectional area is larger than 3.0 $cm^2$, a cell suspension flowed into the cell suspension processing system may not efficiently flow into the hollow fiber separation membranes. The "total cross-sectional area of the hollow fiber separation membranes" refers to the total cross-sectional area of the lumens of hollow fiber separation membranes in the cell suspension processing system, and is determined as follows: (total cross-sectional area)=(number of fibers)×π×(hollow fiber inner diameter)×(hollow fiber inner diameter).

The cell suspension processing system according to the present invention may be sterilized. The sterilization may be accomplished by any method without limitation, and common sterilization techniques for medical devices, such as γ-ray sterilization, electron beam sterilization, EOG sterilization, and high-pressure vapor sterilization, can be employed.

Examples of cells that can be concentrated by the present invention include living pluripotent stem cells, such as induced pluripotent stem cells (iPS cells), embryonic stem cells (ES cells), mesenchymal stem cells, mesenchymal cells from fat, mesenchymal stromal cells from fat, pluripotent adult stem cells, bone marrow stroma cells, and hematopoietic stem cells; lymphocytes, such as T cells, B cells, killer T cells (cytotoxic T cells), NK cells, NKT cells, and regulatory T cells; macrophages, monocytes, dendritic cells, granulocytes, red blood cells, and platelets; somatic cells, such as nerve cells, muscle cells, fibroblasts, liver cells, and myocardial cells; and cells engineered by gene transfer and differentiated cells.

In particular, the method is suitable for the production of concentrates of immune cells, such as granulocytes, T cells, B cells, killer T cells (cytotoxic T cells), NK cells, NKT cells, regulatory T cells, macrophages, and dendritic cells.

The cell suspension used in the present invention may be any suspension containing cells without limitation, and examples thereof include suspensions obtained from living tissues, such as fat, skin, blood vessels, cornea, buccal tissue, kidney, liver, pancreas, heart, nerve, muscle, prostate, intestines, amnion, placenta, and umbilical cord, through treatments, such as enzyme treatment, disruption, extraction, decomposition, and/or ultrasonic treatment. Other examples include cell suspensions prepared from blood or bone marrow through pre-treatments, such as density gradient centrifugation, filtration, enzyme treatment, decomposition, and/or ultrasonic treatment. Further examples include cell suspensions obtained by culturing such cells as described above, in vitro using culture fluid, for example, DMEM, α-MEM, MEM, IMEM, or RPMI-1640, or using stimulation factors, such as cytokines, antibodies or peptides, or the like.

Cell concentrates produced using the cell suspension processing system may be further washed. The "washing" means to replace a biological fluid or medium in which cells are suspended with a liquid free from cells, such as physiological saline or an infusion solution. This removes unnecessary components in concentrates, and thus provides concentrates suitable for use in implantation to human and animals.

Suitable examples of cell-free liquids usable in the washing include physiological saline, infusion solutions, media, distilled water, inorganic salts, saccharides, serum, protein-containing liquids, buffers, media, plasma, and other cell-free liquids. In particular, physiological saline and infusion solutions are preferred for safety reasons.

The present invention can separate cells for use in, but not limited to, the treatment of leukemia, regeneration of the heart muscle or blood vessels, treatment of diseases such as stem cell deficiency, bone diseases, cartilage diseases, ischemic diseases, vascular diseases, neuropathies, burns, chronic inflammation, cardiac diseases, immunodeficiency disorders, and Crohn's disease, tissue engineering (e.g. tissue enlargement for breast implant, wrinkle reduction, cosmetic surgery, and treatment of tissue depression), immunotherapies (e.g. T cell therapy, NKT cell therapy, and dendritic cell implantation), and gene therapies using gene-transferred cells. Isolated cells may be seeded on a structure such as a scaffold prior to use in therapy.

Cell concentrates obtained using the cell suspension processing system may be further cultured. The culturing following the washing for replacing biological fluids or media in which cells are suspended allows for an increase of the number of cells, differentiation of cells, transformation of cells, and introduction of a gene, for example. Examples of media used to grow cells include DMEM, α-MEM, MEM, IMEM, and RPMI-1640. Stimulation factors, such as cytokines, antibodies and peptides, may also be used for the culture.

A pharmaceutical composition can be produced by concentrating cells according to the above method for producing a cell concentrate, and mixing the concentrated cells with a pharmaceutically acceptable additive. Examples of pharmaceutically acceptable additives include anticoagulants, nutritional supplements (e.g. vitamins), and antibiotics.

Cell concentrates produced using the cell suspension processing system may be further cryopreserved. Liquid nitrogen is preferably used for the cryopreservation because it causes less damage. Cryopreserved cells may be melted for use in implantation to human and animals or studies, or may be melted to be cultured again. Since the concentration process causes less damage on cells, cells concentrated by the above method are suitably used in their applications even after being cryopreserved and melted.

The following illustrates an exemplary method for separating cells using the cell suspension processing system according to the present invention, but the present invention is not limited only to this example. Various modifications within the scope of the present invention are possible.

In the process of separating (concentrating) cells from a cell suspension using a cell suspension processing system according to the present invention, a cell suspension is flowed into the hollow fiber separation membranes in the cell suspension processing system, a substantially cell-free filtrate is removed from the cell suspension to the outside of the hollow fiber separation membranes by inside-out filtration, and a cell-enriched cell suspension is then flowed out of the cell suspension outlet port. The "substantially cell-free filtrate" herein refers to a filtrate in which the number of cells present therein is not more than 0.1% of that of the original cell suspension.

First, tubes or the like are attached to the cell suspension inlet and outlet ports of the cell suspension processing system (these tubes partially constitute a path of a cell suspension flowing into and out of the hollow fibers in the processing system), and further connected to a container (e.g. a cell suspension-containing cell bag) such that a cell suspension can circulate between the container (e.g. bag) and the cell suspension processing system. In order to circulate the suspension, a machine, such as a pump, may be contemplated to be provided in the path. Moreover, tubes connected to a waste tank or the like are preferably connected to the filtrate outlet ports. In this case, the entire path is preferably installed in an aseptic environment. Moreover, in this case, an area of the path near the cell suspension outlet port may be designed thinner to apply pressure to the separation membranes, or filtration may be performed while applying pressure to the tube on the filtrate side using a pump or the like. Any of various filtration techniques generally used with hollow fiber separation membranes can be used in combination.

After a suspension is concentrated to a certain degree, a washing solution (e.g. a buffer) may be added, and the concentration process may be repeated to wash cells and replace the medium. At this time, additional washing solution is introduced from an inlet port which is provided to a tube connected to the circulating path, preferably from an inlet port through which a solution is aseptically introduced.

The concentrated and washed cell suspension can be recovered in a recovery bag or the like, and used for applications such as treatments. Preferably, the recovery bag is aseptically connected to an additional outlet port, such as a three-way stopcock, which is connected to a tube of the circulating path.

EXAMPLES

The following shows experimental results for demonstrating the present invention. The "cell recovery rate" herein refers to the quotient of the division of the total number of cells in a cell suspension concentrated to a certain degree by the initial number of cells. A larger recovery rate corresponds to better recovery efficiency. The "viability ratio" is defined as the quotient of the division of the viability after the processing by the viability before the processing, wherein the viability is calculated by dividing the number of undyed living cells counted after trypan blue staining, excluding dead cells dyed with trypan blue, by the total number of cells. In the examples below, the number of cells was determined from the amount of a cell suspension and the cell concentration, which was defined as the cell concentration in a white blood cell fraction, by analyzing the cell suspension with a blood cell counter (Sysmex Corp., K-4500).

In the following examples, cells were concentrated as follows. Vinyl chloride tubes were connected to the inlet port and outlet port of the cell suspension processing system of each example. A cell suspension was accumulated in a plastic container, and the ends of the vinyl chloride tubes extending from both ends of the cell suspension processing system were immersed in the suspension to allow the suspension to circulate through the module and tubes. Pumps were connected to the vinyl chloride tubes to appropriately control the velocity of the suspension. Additional tubes were attached to the filtrate outlet ports of the cell suspension processing system to discharge a filtrate to a waste container. The cell suspension was circulated through the path at a certain velocity under the control of the pumps, and thereby filtrated. After the cell suspension was concentrated to a certain amount, remaining cell suspension in the tubes and the hollow fiber separation membranes was flushed out with air, the pumps were turned off, and the number of cells present in the cell suspension in the plastic container was determined to calculate the recovery rate. In the experiments in the following examples, a commercial hollow fiber separation membrane module was used as the cell suspension processing system according to the present invention.

Example 1

An experiment of concentrating cells was performed using hollow fiber separation membranes made of polyethersulfone [model No.: M2-M02E-300-F1N (Spectrum Laboratories), filtration area: 0.31 m$^2$, pore size: 0.2 µm, cross-sectional area: 1.737 cm$^2$]. The average pore size of the inner pores of the hollow fiber separation membranes was found to be 5.57 µm from a 2000×SEM image. Cultured Jurkat cells were suspended in RPMI 1640 medium (10% FBS). A 1500 mL portion of this cell suspension (concentration: approximately 2.0×10$^6$ cells/mL) was sampled, and the medium was filtered. The sample was loaded at a flow rate of 200 mL/min to provide an initial filtrate flow rate of 181 mL/m$^2$/min. The cell recovery rate was found to be 84%, and the viability ratio was found to be 97%.

Example 2

The same separation membranes as those used in Example 1 were used. A sample was loaded at a flow rate of 555 mL/min to provide an initial filtrate flow rate of 425 mL/m$^2$/min. The cell recovery rate was found to be 81%, and the viability ratio was found to be 95%.

Example 3

The same separation membranes as those used in Example 1 were used. A sample was loaded at a flow rate of 650 mL/min to provide an initial filtrate flow rate of 250 mL/m²/min. The cell recovery rate was found to be 92%, and the viability ratio was found to be 99%.

Example 4

The same separation membranes as those used in Example 1 were used. A sample was loaded at a flow rate of 830 mL/min to provide an initial filtrate flow rate of 645 mL/m²/min. The cell recovery rate was found to be 91%, and the viability ratio was found to be 99%.

Example 5

The same separation membranes as those used in Example 1 were used. A sample was loaded at a flow rate of 1000 mL/min to provide an initial filtrate flow rate of 1290 mL/m²/min. The cell recovery rate was found to be 93%, and the viability ratio was found to be 98%.

Comparative Example 1

The same separation membranes as those used in Example 1 were used. A sample was loaded at a flow rate of 360 mL/min to provide an initial filtrate flow rate of 645 mL/m²/min. The cell recovery rate was found to be 60%, and the viability ratio was found to be 98%.

Comparative Example 2

The same separation membranes as those used in Example 1 were used. A sample was loaded at a flow rate of 520 mL/min to provide an initial filtrate flow rate of 857 mL/m²/min. The cell recovery rate was found to be 53%, and the viability ratio was found to be 99%.

Example 6

An experiment of concentrating cells was performed using hollow fiber separation membranes made of polyethersulfone [model No.: M2-M05E-300-F1N (Spectrum Laboratories), filtration area: 0.31 m², pore size: 0.5 μm, cross-sectional area: 1.737 cm²]. The average pore size of inner pores of the hollow fiber separation membranes was found to be 3.86 μm from a 2000×SEM image. Cultured Jurkat cells were suspended in RPMI 1640 medium (10% FBS). A 1500 mL portion of this cell suspension (concentration: approximately 2.0×10⁶ cells/mL) was sampled, and the medium was filtered. The sample was loaded at a flow rate of 660 mL/min to provide an initial filtrate flow rate of 510 mL/m²/min. The cell recovery rate was found to be 81%, and the viability ratio was found to be 93%.

Example 7

The same separation membranes as those used in Example 6 were used. A sample was loaded at a flow rate of 730 mL/min to provide an initial filtrate flow rate of 390 mL/m²/min. The cell recovery rate was found to be 91%, and the viability ratio was found to be 96%.

Example 8

The same separation membranes as those used in Example 6 were used. A sample was loaded at a flow rate of 750 mL/min to provide an initial filtrate flow rate of 1074 mL/m²/min. The cell recovery rate was found to be 90%, and the viability ratio was found to be 99%.

Comparative Example 3

The same separation membranes as those used in Example 6 were used. A sample was loaded at a flow rate of 750 mL/min to provide an initial filtrate flow rate of 1378 mL/m²/min. The cell recovery rate was found to be 33%, and the viability ratio was found to be 94%.

Example 9

An experiment of concentrating cells was performed using hollow fiber separation membranes made of polyethersulfone [model No.: M2-M02E-100-F1N (Spectrum Laboratories), filtration area: 0.105 m², pore size: 0.2 μm, cross-sectional area: 0.588 cm²]. The same hollow fibers as those used in Example 1 were used. Cultured Jurkat cells were suspended in RPMI 1640 medium (10% FBS). A 1500 mL portion of this cell suspension (concentration: approximately 2.0×10⁶ cells/mL) was sampled, and the medium was filtered. The sample was loaded at a flow rate of 600 mL/min to provide an initial filtrate flow rate of 1002 mL/m²/min. The cell recovery rate was found to be 102%, and the viability ratio was found to be 100%.

Example 10

The same separation membranes as those used in Example 9 were used. A sample was loaded at a flow rate of 600 mL/min to provide an initial filtrate flow rate of 1511 mL/m²/min. The cell recovery rate was found to be 96%, and the viability ratio was found to be 97%.

Example 11

The same separation membranes as those used in Example 9 were used. A sample was loaded at a flow rate of 600 mL/min to provide an initial filtrate flow rate of 2116 mL/m²/min. The cell recovery rate was found to be 88%, and the viability ratio was found to be 99%.

Comparative Example 4

The same separation membranes as those used in Example 9 were used. A sample was loaded at a flow rate of 620 mL/min to provide an initial filtrate flow rate of 3174 mL/m²/min. The cell recovery rate was found to be 76%, and the viability ratio was found to be 98%.

Example 12

An experiment of concentrating cells was performed using hollow fiber separation membranes made of polyethylene [model No.: PSP-103 (Asahi Kasei Chemicals Corp.), filtration area: 0.17 m², pore size: 0.1 μm, cross-sectional area: 1.510 cm²]. The average pore size of inner pores of the hollow fiber separation membranes was found to be 0.75 μm from a 5000×SEM image. Cultured Jurkat cells were suspended in RPMI 1640 medium (10% FBS). A 1500 mL portion of this cell suspension (concentration: approximately 2.0×10⁶ cells/mL) was sampled, and the medium was filtered. The sample was loaded at a flow rate of 200 mL/min to provide an initial filtrate flow rate of 315 mL/m²/min. The cell recovery rate was found to be 83%, and the viability ratio was found to be 100%.

Example 13

The same separation membranes as those used in Example 12 were used. A sample was loaded at a flow rate of 820 mL/min to provide an initial filtrate flow rate of 1262 mL/m²/min. The cell recovery rate was found to be 88%, and the viability ratio was found to be 98%.

Comparative Example 5

The same separation membranes as those used in Example 12 were used. A sample was loaded at a flow rate of 480 mL/min to provide an initial filtrate flow rate of 1336 mL/m²/min. The cell recovery rate was found to be 62%, and the viability ratio was found to be 99%.

Example 14

An experiment of concentrating cells was performed using hollow fiber separation membranes made of polysulfone [model No.: M20S-300-01P (Spectrum Laboratories), filtration area: 0.31 cm², pore size: 0.05 μm, cross-sectional area: 1.737 cm²]. The average pore size of inner pores of the hollow fiber separation membranes was found to be 2.44 μm from a 2000×SEM image. Cultured Jurkat cells were suspended in RPMI 1640 medium (10% FBS). A 1500 mL portion of this cell suspension (concentration: approximately $2.0 \times 10^6$ cells/mL) was sampled, and the medium was filtered. The sample was loaded at a flow rate of 820 mL/min to provide an initial filtrate flow rate of 716 mL/m²/min. The cell recovery rate was found to be 91%, and the viability ratio was found to be 99%.

Example 15

The same separation membranes as those used in Example 14 were used. A sample was loaded at a flow rate of 800 mL/min to provide an initial filtrate flow rate of 1075 mL/m²/min. The cell recovery rate was found to be 87%, and the viability ratio was found to be 99%.

Comparative Example 6

The same separation membranes as those used in Example 14 were used. A sample was loaded at a flow rate of 810 mL/min to provide an initial filtrate flow rate of 1489 mL/m²/min. The cell recovery rate was found to be 79%, and the viability ratio was found to be 92%.

TABLE 1

| | Example 1 | Example 2 | Example 3 | Example 4 | Example 5 | Comparative Example 1 | Comparative Example 2 |
|---|---|---|---|---|---|---|---|
| Hollow fiber material | Polyethersulfone | | | | | | |
| Membrane area (m²) | 0.31 | | | | | | |
| Nominal pore size (μm) | 0.2 | | | | | | |
| Cross-sectional area (cm²) | 1.737 | | | | | | |
| Flow rate (ml/min) | 200 | 550 | 650 | 830 | 1000 | 360 | 520 |
| Linear velocity (cm/min) | 115 | 316 | 374 | 477 | 575 | 207 | 299 |
| Initial filtrate flow rate (ml/m²/min) | 181 | 425 | 250 | 645 | 1290 | 645 | 857 |
| Initial filtrate flow rate/linear velocity | 1.57 | 1.34 | 0.66 | 1.35 | 2.24 | 3.11 | 2.86 |
| Average pore size of inner pores of hollow fibers (μm) | 5.57 | | | | | | |
| Cell recovery rate | 84% | 81% | 92% | 91% | 93% | 60% | 53% |
| Viability ratio | 97% | 95% | 99% | 99% | 98% | 98% | 99% |

| | Example 6 | Example 7 | Example 8 | Comparative Example 3 | Example 9 | Example 10 | Example 11 | Comparative Example 4 |
|---|---|---|---|---|---|---|---|---|
| Hollow fiber material | Polyethersulfone | | | | | | | |
| Membrane area (m²) | 0.31 | | | | | | 0.105 | |
| Nominal pore size (μm) | 0.5 | | | | | | 0.2 | |
| Cross-sectional area (cm²) | 1.737 | | | | | | 0.588 | |
| Flow rate (ml/min) | 660 | 730 | 750 | 750 | 600 | 600 | 600 | 620 |
| Linear velocity (cm/min) | 379 | 420 | 431 | 431 | 1020 | 1020 | 1020 | 1054 |
| Initial filtrate flow rate (ml/m²/min) | 510 | 390 | 1074 | 1378 | 1002 | 1511 | 2116 | 3174 |
| Initial filtrate flow rate/linear velocity | 1.34 | 0.92 | 2.49 | 3.19 | 0.98 | 1.48 | 2.07 | 3.01 |
| Average pore size of inner pores of hollow fibers (μm) | 3.86 | | | | | | — | |
| Cell recovery rate | 81% | 91% | 90% | 33% | 102% | 96% | 88% | 76% |
| Viability ratio | 93% | 96% | 99% | 94% | 100% | 97% | 99% | 98% |

TABLE 2

| | Example 12 | Example 13 | Comparative Example 5 | Example 14 | Example 15 | Comparative Example 6 |
|---|---|---|---|---|---|---|
| Hollow fiber material | Polyethylene | | | Polysulfone | | |
| Hollow fiber inner diameter (mm) | 0.7 | | | 0.5 | | |
| Membrane area (m²) | 0.17 | | | 0.31 | | |
| Nominal pore size (μm) | 0.1 | | | 0.05 | | |
| Cross-sectional area (cm²) | 1.510 | | | 1.737 | | |

TABLE 2-continued

|  | Example 12 | Example 13 | Comparative Example 5 | Example 14 | Example 15 | Comparative Example 6 |
|---|---|---|---|---|---|---|
| Flow rate (ml/min) | 200 | 820 | 480 | 820 | 800 | 810 |
| Linear velocity (cm/min) | 132 | 543 | 317 | 472 | 460 | 466 |
| Initial filtrate flow rate (ml/m²/min) | 315 | 1262 | 1336 | 716 | 1075 | 1489 |
| Initial filtrate flow rate/ linear velocity | 2.38 | 2.32 | 4.21 | 1.51 | 2.33 | 3.19 |
| Average pore size of inner pores of hollow fibers (μm) |  | 0.75 |  |  | 2.44 |  |
| Cell recovery rate | 83% | 88% | 62% | 91% | 87% | 79% |
| Viability ratio | 100% | 98% | 99% | 99% | 99% | 92% |

As seen in Table 1, cell suspensions can be highly efficiently concentrated regardless of the total lumen cross-sectional area and the membrane area of the hollow fiber separation membranes when the quotient of the division of the initial filtrate flow rate by the linear velocity of a cell suspension flowing through the hollow fibers is 2.5 or less. Additionally, Tables 1 and 2 reveal that cells can be more efficiently concentrated when the average pore size of inner pores of the hollow fiber separation membranes is within the range of from 0.1 μm to 10 μm, and the quotient of the division of the initial filtrate flow rate by the linear velocity of a cell suspension flowing through the hollow fibers is 2.5 or less.

Accordingly, as demonstrated by the examples, by using a hollow fiber separation membrane provided with inner pores with an average pore size within the range of from 0.1 μm to 10 μm, and flowing a cell suspension through hollow fibers such that the quotient of the division of the initial filtrate flow rate by the linear velocity of the cell suspension is 2.5 or less, cells can be highly efficiently recovered while unnecessary components other than the cells, such as proteins, in the cell suspension are removed, and cell concentrates can be provided without causing pores of hollow fibers to be clogged. Additionally, it was revealed that by avoiding washing processes or the like that cause damage on cells, cells are less damaged, thereby increasing the viability of cells.

Therefore, the method of the present invention can efficiently concentrate only target cells by aseptic operations. This method does not use hollow fibers of different kinds and thus can prevent leakage of the materials. Namely, this method ensures high safety and provides cells for use in cell therapy.

REFERENCE SIGNS LIST

1. Tubular housing
2. Body
3. Head
4. Filtrate outlet port
5. Bundle of hollow fiber separation membranes
6. Open end (indicated by dots)
7. Resin layer (hatched area)
8a. Cell suspension inlet port
8b. Cell suspension outlet port
9. Header

The invention claimed is:

1. A method for producing a cell concentrate, the method comprising:
   processing a human or animal cell suspension with an inside-out filtration system at a linear velocity of the cell suspension of 115 to 1020 cm/min, and at an initial filtrate flow rate,
   wherein the system comprises:
   a cell suspension inlet port; a filtrate outlet port; a cell suspension outlet port; and a hollow fiber separation membrane interposed between the cell suspension inlet port and the cell suspension outlet port,
   wherein the hollow fiber separation membrane has inner pores with an average pore size of from 0.1 μm to 0.5 μm, and
   a quotient of a division of the initial filtrate flow rate by the linear velocity of the cell suspension flowing through the hollow fibers is 2.5 or less.

2. The method according to claim 1,
   wherein the cell suspension flows through the cell suspension inlet port at a flow rate of from 200 mL/min to 1200 mL/min.

3. The method according to claim 1,
   wherein the hollow fiber separation membrane comprises a synthetic polymer material.

4. The method claim 1,
   wherein the hollow fiber separation membrane comprises a polysulfone or polyolefin polymer material.

5. The method according to claim 1,
   wherein the hollow fiber separation membrane comprises polyethersulfone, polysulfone, or polyethylene.

6. The method according to claim 1,
   wherein the cell suspension is an immune cell suspension.

7. The method according to claim 1, further comprising washing cells of the cell suspension.

8. A method for growing cells, the method comprising:
   producing a cell concentrate, comprising processing a human or animal cell suspension with an inside-out filtration system at a linear velocity of the cell suspension of 115 to 1020 cm/min, and at an initial filtrate flow rate,
   wherein the system comprises:
   a cell suspension inlet port; a filtrate outlet port; a cell suspension outlet port; and a hollow fiber separation membrane interposed between the cell suspension inlet port and the cell suspension outlet port,
   wherein the hollow fiber separation membrane has inner pores with an average pore size of from 0.1 μm to 5 μm, and
   a quotient of a division of the initial filtrate flow rate by the linear velocity of the cell suspension flowing through the hollow fibers is 2.5 or less; and
   mixing the cell concentrate with a medium.

9. A method for cryopreserving cells, the method comprising:
   producing a cell concentrate, comprising processing a human or animal cell suspension with an inside-out filtration system at a linear velocity of the cell suspension of 115 to 1020 cm/min, and at an initial filtrate flow rate, wherein the system comprises:

a cell suspension inlet port: a filtrate outlet port: a cell suspension outlet port; and a hollow fiber separation membrane interposed between the cell suspension inlet port and the cell suspension outlet port, wherein the hollow fiber separation membrane has inner pores with an average pore size of from 0.1 μm to 5 μm, and a quotient of a division of the initial filtrate flow rate by the linear velocity of the cell suspension flowing through the hollow fibers is 2.5 or less; and cryopreserving a cell concentrate obtained by the production method according to claim 1, with liquid nitrogen.

10. A method for cryopreserving cells, the method comprising:

cryopreserving a cell obtained by the cell growth method according to claim 8, with liquid nitrogen.

\* \* \* \* \*